Figure 1:
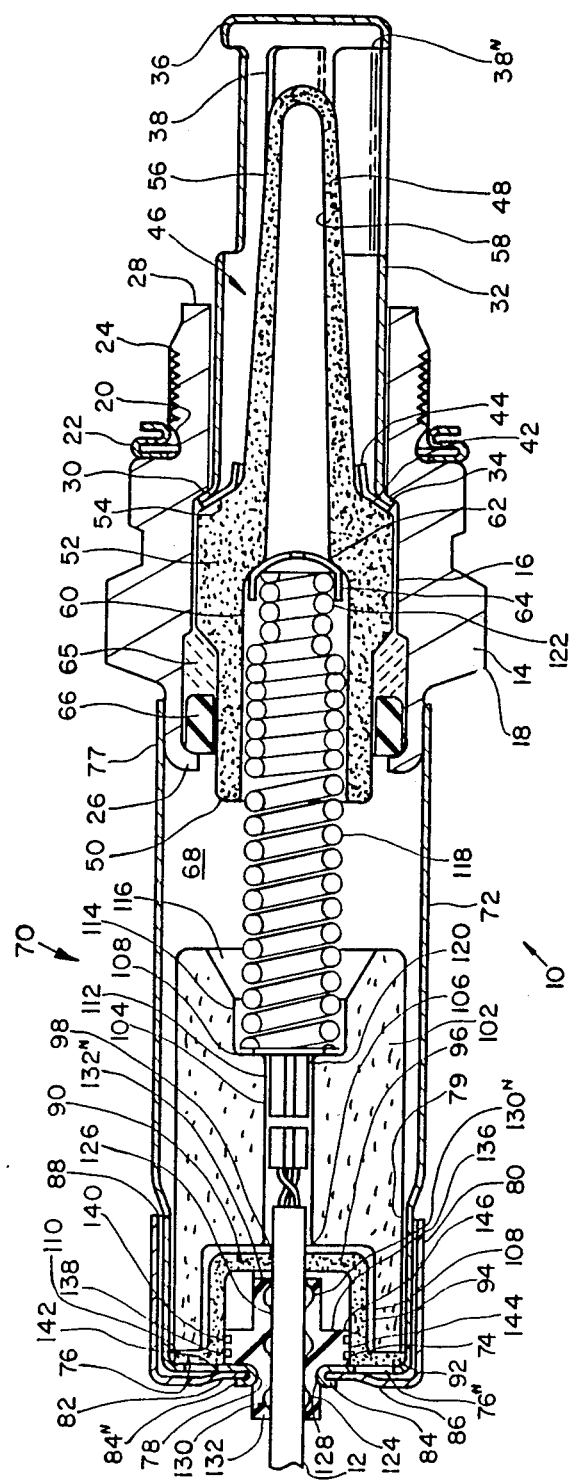

United States Patent [19]

Barbieri et al.

[11] Patent Number: 4,786,397
[45] Date of Patent: Nov. 22, 1988

[54] SEAL FOR SINGLE WIRE O₂ SENSOR

[75] Inventors: Michael G. Barbieri; Harry P. Wertheimer, both of Findlay, Ohio

[73] Assignee: Allied-Signal Inc., Morristown, N.J.

[21] Appl. No.: 107,619

[22] Filed: Oct. 9, 1987

[51] Int. Cl.⁴ .............................................. G01N 27/46
[52] U.S. Cl. ................................. 204/427; 204/424; 204/428
[58] Field of Search ........................ 204/15, 421–429

[56] References Cited

U.S. PATENT DOCUMENTS

| | | | |
|---|---|---|---|
| 3,720,594 | 3/1973 | Wilson | 204/15 |
| 4,219,399 | 8/1980 | Gruner et al. | 204/428 |
| 4,323,440 | 4/1982 | Akatsuka | 204/428 |
| 4,597,849 | 7/1986 | Burkhardt et al. | 204/424 |
| 4,717,464 | 1/1988 | Oshima et al. | 204/427 |

Primary Examiner—T. Tung
Attorney, Agent, or Firm—Leo H. McCormick, Jr.; Ken C. Decker

[57] ABSTRACT

An oxygen sensor (10) having an electrolyte sensor (40) located in a metal shell (14) and an insulating terminal (102) located in a metal sleeve (72). The metal sleeve (72) is secured to the metal shell (14) to define a reference chamber (68) adjacent the interior of the electrolyte sensor (46). A closed end (74) on the sleeve (72) has a plurality of openings (76, 76¹ . . . 76ⁿ) surrounding a central opening (78). A porous filter (90) has a base (92) that is continually urged against end (74) by the action of spring (118) on terminal (102). A grommet (124) located in the central opening (78) has a cylindrical body with a flange (136) that radially engages filter (90) and a series of lands (132, 132¹ or 132ⁿ) that form a plurality of sealing surfaces on lead (12) that connects the electrolyte sensor (46) with a controller. Changes in temperature which cause the components of sensor (10) to expand and contract at different rates are compensated by the grommet (124) and filter (90) to assure that water does not enter the reference chamber (68) through the openings in the closed end (74).

4 Claims, 2 Drawing Sheets

SEAL FOR SINGLE WIRE O₂ SENSOR

This invention relates to a seal for a single wire O₂ sensor. A grommet located on an axial opening of a metal shell has a series of inner peripheral surfaces that engage the single wire and a series of outer peripheral surfaces that engage a porous vent seal. The vent seal is resiliently positioned adjacent openings in a metal shell to prevent the entry of water into a reference chamber of the O₂ sensor. A cap which surrounds the metal shell allows air to be communicated to the openings while protecting the openings from being damaged or exposed to other environmental conditions that may effect the communication of air to the reference chamber.

Oxygen sensors detect the oxygen concentration of exhaust gas from an internal combustion engine of a vehicle through the change in electrical potential generated across an ion-transferable solid electrolyte. The solid electrolyte which is usually in the shape of a thimble has a first side exposed to the exhaust gas and a second side exposed to a reference gas. Initially, the reference gas was transferred to the second side through a hole in the side of a shield. Under operating conditions the solid electrolyte can reach a temperature of 700° to 800° C. As long a the oxygen sensor is dry environment the solid electrolyte operates in a satisfactory manner. Unfortunately in some vehicles, the oxygen sensors are located in a location wherein water may be communicated to the solid electrolyte. If water touches the solid electrolyte when it is in operation, quenching occurs with cracks developing on the surface of the thimble. Such cracks adversely affect the operation of the oxygen sensor.

In U.S. Pat. No. 4,127,464 the reference gas is carried into a sealed shield through stranded wire core surrounded by an insulating jacket retained in a end cap. The reference gas is brought from a remote area where water is not present to assure the only dry reference air is presented to the solid electrolyte. This invention while solving the entry of water to the reference chamber has not met with success since the cost of the stranded wire core cannot be relied upon as the sole source of reference gas in all cases.

In the invention disclosed herein, a porous seal is axially urged into engagement with the metal shield while a resilient grommet, that surrounds a lead connecting a solid electrolyte to a controller radially engages the porous seal to seal the reference chamber from the entry of water. The metal shield has a first diameter section adjacent a closed end and a second diameter section which is attached to a carrier in which the solid electrolyte thimble is located. The closed end has a series of openings or vent holes through which air is communicated to the reference chamber and a central opening for the grommet. A cap member concentric to the first diameter of the metal shield has an offset to define a flow path for reference air to the vent holes. Thus, the solid electrolyte thimble is only presented with dry reference air.

An object of the present invention is to provide an oxygen sensor with a seal which permits reference air to be presented to a solid electrolyte thimble while excluding water from a reference chamber.

An object of this invention is to seal a reference chamber from water while allowing air to pass through a porous filter. The filter is axially held against an end member of a metal shield by a terminal member and radially positioned by a grommet to assure that vent holes in the metal shield are hermetically sealed to prevent water from entering the reference chamber.

A further object of this invention is to provide an oxygen sensor with dry reference air from adjacent the oxygen sensor.

These objects should be apparent from reading this specification while viewing the drawing.

Figure 2:
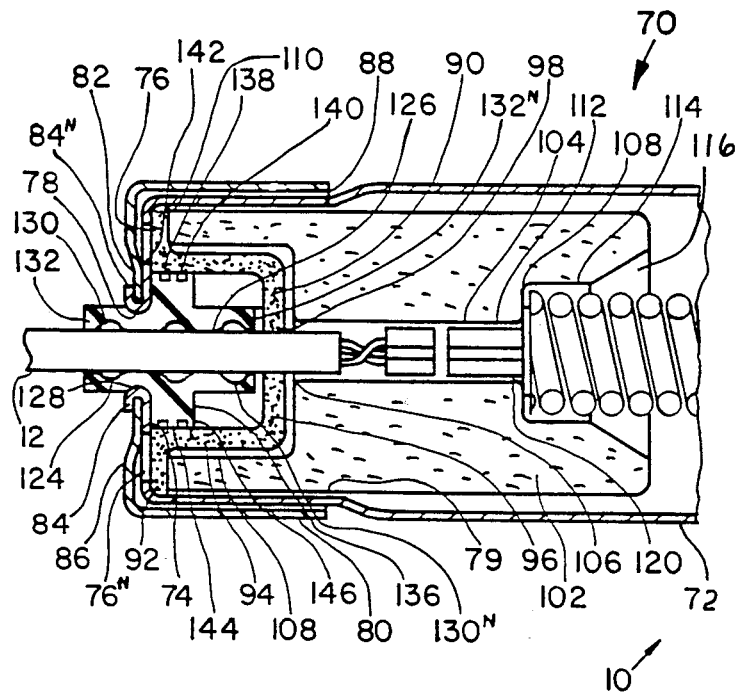

FIG. 1 of the drawing is a schematic sectional view of an oxygen sensor having a sealed reference chamber made according to the principles of this invention and FIG. 2 is an enlarged view of the seal and filter arrangment of FIG. 1.

The electrochemical sensor 10 is located in the exhaust pipe of a vehicle and supplies a controller in a fuel metering system with an indication of the oxygen content is the exhaust gases. Changes in the oxygen content in the exhaust gases are experienced by sensor 10 and transmitted by wire or lead 12 to the controller to maintain the air/fuel ratio supplied to operate the engine of the vehicle within set clean air standards.

Sensor 10 has a metal shell 14 with an axial bore 16 therein. Shell 14 has a groove 20 for retention of a washer 22. Shell 14 has a hexagonal surface 18 located adjacent the first end 26 thereof. A tool is designed to engage hexagonal surface 18 to install the oxygen sensor 10 in a tail pipe when threads 24 are screwed into a boss in the tail pipe. The washer 22 engages the boss to establish a seal which prevents the exhaust gases from escaping from the tail pipe. Metal shell 14 has an annular shoulder 30 located in bore 16 between a first end 26 and a second end 28.

A vented protective shield 32 has a first end 34 and a second end 36. The first end 34 has a flange which is seated on should 30 when shield 32 is inserted in bore 16. A plurality of openings 38, 38' . . . 38$^n$ located adjacent end 36 allow exhaust gases to be freely communicated into the interior 40 of the shield 32 when located in an exhaust pipe.

A carrier member 42 is placed in bore 16 and engages the flange on shield 32. Carrier member 42 has an inwardly projecting conical lip 44 which extends an electrical ground formed between the tail pipe and metal shell 14 to the interior of bore 16.

A sensor element 46 in the form of a tubular thimble is inserted into bore 16. The thimble has a closed end 48 and an opened end 50. An annular rib 52 on the peripheral surface of sensor element 46 has a shape that substantially matches bore 16. Rib 52 is connected to the closed end 48 by a conical surface 54 that engages carrier 44. The sensor element 46 is made of an ion conductive solid electrolyte such a zirconium dioxide and has an external surface 56 and an internal surface 58 coated with a porous electron conductive layer of platinum to form a catalyst for exhaust gases presented to these surfaces. The external coating extends from approximately conical surface 54 to the closed end 48 while the internal coating extends from the interior of the closed end 48 to a location 60 above a contact point 62 for a dome shaped disc 64.

A quantity of talc powder 65 is placed in bore 16 between rib 52 and end 50 and a talc ring 66 placed on top of the powder. Thereafter end 26 is rolled over the ring to retain the sensor element 46 in the metal shell 14. The talc powder and talc ring established a seal to assure that bore 16 is sealed and exhaust gases do not escape from the tail pipe into a reference chamber 68 formed when terminal retaining member 70 is attached to the metal shell 14.

Terminal retaining member 70 has a sleeve or shield 72 with a closed end 74 and an opened end 77. End 77 surrounds the peripheral surface of the metal shell 14 and is fixed thereto by a weld or bond to establish an air tight seal. End 74 has a series of openings or vent holes 76 ... $76^n$ which surrounds a central opening 78. Sleeve 72 has a necked down section 79 adjacent end 74. A protective member 80 concentric to the necked down section 70 has an annular end section 82 that engages end 74. A series of tabs 84, 84' ... $84^n$ extend from the end member 74 to hold section 82 against end 74. In some instances tabs 84 will be a continuous member that is rolled over the end of section 82. Section 82 has an offset 86 such that a continuous protected flow path 88 is defined for environmental air along the necked down section 79 to the vent holes 76, 76'. ... $76^n$.

A porous filter material 90 sold under the trade name of Zitex by Norton Chemplast, or an equivalent material which allows air to flow through while excluding water has an annular base 92 located adjacent to and completely over the vent holes 76, 76' ... $76^n$. A cylindrical section 94 which extends from the base 92 has an internal projecting lip 96. Lip 96 forms an axial opening 98 through which wire 12 is brought into chamber 68. An insulator member 102 has a cylindrical body that is concentric to the necked down section 79 of sleeve or shield 72 with an axial bore 104. Bore 104 has a first diameter 108 that extends from end 110 to a first shoulder 106, a second diameter 112 that extends from the first shoulder 106 to a second shoulder 108 and a third diameter 114 extends to a conical section 116. The cylindrical projection 94 of the porous filter 90 extends into bore 104 to a position adjacent the first shoulder 106 while spring 118 extends into the third diameter 114 of bore 104 to engage terminal 120 on the end of wire 100. Spring 118 has a tip 122 that matches the shape of contact disc 64 to complete an electrical flow path between the inside surface 58 of the sensor element 46 and terminal 120.

A grommet 124 has a cylindrical body with an axial bore 126. A groove 128 on the peripheral surface of the cylindrical body forms a seat for tabs or flange 84 while a series of grooves 130, 130' ... $130^n$ in bore 126 define lands 132, 132' ... $132^n$ which act on the insulative jacket of wire 12 to form a series of sealing surfaces. An annular flange 136 extends from the peripheral surface of the cylindrical body adjacent groove 128 and radially engages the interior surface of the cylindrical projection 94 of the porous filter 90. Flange 136 has grooves 138 and 140 on its surface to separate lands 142, 144 and 146 from each other. Lands 142, 144 and 146 establish separate radial sealing surfaces with the porous filter 90.

During the operation of an internal combustion engine, exhaust gases are carried from the exhaust pipe through openings 38, 38' ... $38^n$ in shield 32 to surface 56 on sensor element 46. At the same time, air from the environment is carried along flow path 88 to vent holes 76, 76' ... $76^n$ and passes through filter 90 to thereafter be communicated through bore 104 to reference chamber 68 for presentation to the interior surface 58 of sensor element 46. Changes in ion flow between the exterior conductive surface 56 and the interior conductive surface 58 generates an operational signal which is carried by wire 12 to a controller associated with the fuel system wherein the fuel/air ratio is modified to maintain the operation of the engine within set standards.

Under operating conditions, the temperature that the sensor element is exposed to can reach 400° C. The metal shell 14, sleeve 72 and spring 118 have substantially the same coefficient of expansion while the sensor element 46 and insulator 102 have the same coefficient of expansion. Spring 118 provides a constant force that acts through insulator 102 to urge base 92 of filter 90 against end 74 to require air flow through vent holes 76, 76' ... $76^n$. The multiple sealing surfaces 142, 144, and 146 on grommet 124 assure that air is not presented to chamber 68 without passing through filter 90. Thus through this seal and filter structure dry environmental air present at the sensor location is presented to the sensor element to provide a reference gas.

We claim:

1. In an oxygen sensor having a solid electrolyte member located in a metal shell and a terminal retaining member located in a sleeve attached to the metal shell, the terminal retaining member positioning an electrical contact on a corresponding lead which connects the electrolyte member to a controller, said sleeve having an end with tabs surrounding a central opening and with a plurality of other openings, said central opening locating the lead connecting said solid electrolyte with a controller while said plurality of other openings allow environmental air to be communicated to a reference chamber located between the terminal member and solid electrolyte, the improvements comprising:

a porous filter having a base with an annular projection that extends into an axial bore in said terminal, said projection having an inwardly projecting lip that forms an axial opening, said lip engaging and holding said lead in a axial position within said sleeve;

a spring that extends from said solid electrolyte member and acts on said terminal member to axially urge said porous filter into direct engagement with said end of said sleeve; and a seal member having a cylindrical body with a peripheral surface, said peripheral surface having a first groove adjacent a flange, said cylindrical body having a second axial bore with a series of grooves that define a corresponding series of lands, said lead passing through said second axial bore and engaging said series of lands to establish multiple sealing surfaces while said flange engages an interior surface on said annular projection of said porous filter to establish a peripheral radial seal, said tabs on said end of said sleeve being located in said first groove of said seal member to position said seal member with respect to said end of said sleeve, said metal shell, sleeve and terminal member responding to the difference in temperature of exhaust gases presented to the electrolyte member and environmental air by expanding, said spring providing a constant force to hold the base of said porous filter against said plurality of opening to assure that no water is presented to said reference chamber while said multiple sealing surfaces on said seal member assure that environment air presented to said reference chamber passes through said porous filter.

2. In the oxygen sensor as recited in claim 1 wherein said seal member moves with said end of said sleeve in response to dimensional changes created in response to temperature changes, said seal member having a flange that radially engages said filter to maintain a radial seal during said dimensional changes.

3. In the oxygen sensor as recited in claim 2 further including:
a cap member concentric to said end of said sleeve and attached thereto to define with the sleeve a flow path for environmental air to said plurality of openings.

4. In the oxygen sensor as recited in claim 3 wherein said cap member includes:
an offset section to establish a set dimension for the flow path adjacent said plurality of openings.

* * * * *